US008697382B2

(12) United States Patent
Morinaka (10) Patent No.: US 8,697,382 B2
(45) Date of Patent: Apr. 15, 2014

(54) METHOD OF IDENTIFYING METALLO-β-LACTAMASE-PRODUCING BACTERIA

(75) Inventor: Akihiro Morinaka, Kawasaki (JP)

(73) Assignee: Meiji Seika Pharma Co., Ltd., Tokyo-to (JP)

( * ) Notice: Subject to any disclaimer, the term of this patent is extended or adjusted under 35 U.S.C. 154(b) by 9 days.

(21) Appl. No.: 13/260,965

(22) PCT Filed: Mar. 31, 2010

(86) PCT No.: PCT/JP2010/055902
§ 371 (c)(1),
(2), (4) Date: Nov. 22, 2011

(87) PCT Pub. No.: WO2010/114037
PCT Pub. Date: Oct. 7, 2010

(65) Prior Publication Data
US 2012/0064557 A1    Mar. 15, 2012

(30) Foreign Application Priority Data

Mar. 31, 2009   (JP) ................................ 2009-084497

(51) Int. Cl.
*C12Q 1/34*       (2006.01)
*A61K 31/19*      (2006.01)

(52) U.S. Cl.
USPC ............................................. 435/18; 514/574

(58) Field of Classification Search
USPC ............................................. 435/18; 514/574
See application file for complete search history.

(56) References Cited

U.S. PATENT DOCUMENTS

2007/0254332 A1   11/2007   Yagi et al.
2008/0090825 A1   4/2008    Chikauchi et al.

FOREIGN PATENT DOCUMENTS

| JP | 2000-224998 | 8/2000 |
| JP | 2001-299388 | 10/2001 |
| JP | 2003-135093 | 5/2003 |
| WO | 2005/056820 | 6/2005 |
| WO | 2007/034924 | 3/2007 |

OTHER PUBLICATIONS

International Preliminary Report on Patentability and Written Opinion issued Nov. 15, 2011 in International Application No. PCT/JP2010/055902, of which the present application is the national stage.
Japanese Decision of Rejection (with English translation) issued Aug. 2, 2013 in corresponding Japanese Application No. 2011-507269.
International Search Report issued Jun. 15, 2010 in International (PCT) Application No. PCT/JP2010/055902 of which the present application is the national stage.
Tazai Taisei Ryokunokin ni Tsuite, [online], National Institute of Infectious Diseases, Infectious Disease Surveillance Center, Aug. 8, 2006, Retrieved on Jun. 3, 2010, Retrieved from the internet:<URL:http://idsc.nih.go.jp/disease/MDRP/MDRP-7.2b.pdf.>.
Tazai Taisei Ryokunokin (MDRP) Kansensho-Senmonka Muke Joho-, [online], National Institute of Infectious Diseases, Infectious Disease Surveillance Center, Aug. 8, 2006, Retrieved on Jun. 3, 2010, Retrieved from the internet:<URL:http://idsc.nih.go.jp/disease/MDRP/index.html>.
N. Okamoto et al., "Tazai Taisei Ryokunokin ni Okeru Kokin' yaku no Heiyo Koka", Ehime Journal of Medical Technology, vol. 27, pp. 33-38, 2008.
Japanese Office Action (with English translation) issued Apr. 15, 2013 in corresponding Japanese Patent Application No. 2011-507269.
Supplementary European Search Report issued Aug. 29, 2013 in corresponding European Application No. 10 75 8808.

*Primary Examiner* — Chih-Min Kam
(74) *Attorney, Agent, or Firm* — Wenderoth, Lind & Ponack, L.L.P.

(57) ABSTRACT

An object of the present invention is to provide a method of identifying metallo-β-lactamase-producing bacteria, particularly, a method of conveniently identifying an IMP or VIM type. According to the present invention, there is provided a method of detecting metallo-β-lactamase-producing bacteria, comprising spotting a compound (I) onto a surface of a solid medium coated with the bacteria to be tested, spotting 3 types of β-lactam agents at 3 respective positions different from the spot of the compound (I), culturing the solid medium, and then detecting the metallo-β-lactamase-producing bacteria based on the shape of an inhibition zone formed around the spot of each of the β-lactam agents. There is further provided a method of identifying an IMP or VIM type of the metallo-β-lactamase-producing bacteria.

14 Claims, 4 Drawing Sheets

METHOD OF IDENTIFYING METALLO-β-LACTAMASE-PRODUCING BACTERIA

The present application is a 371 national stage of PCT/JP2010/055902, filed Mar. 31, 2010.

TECHNICAL FIELD

The present invention relates to a method of identifying metallo-β-lactamase-producing bacteria, particularly, a method of identifying a type of metallo-β-lactamase-producing bacteria. The present invention also relates to a kit for the identification of metallo-β-lactamase-producing bacteria, and an identification method using the kit.

BACKGROUND ART

Antimicrobial drugs such as carbapenem, new quinolone, and aminoglycoside are used for serious infections caused by opportunistic pathogens such as *Pseudomonas aeruginosa*. However, bacteria that have also acquired resistance to these drugs have been reported in recent years. In Japan, *Pseudomonas aeruginosa* that has acquired resistance to these 3 drugs is called multidrug resistance *Pseudomonas aeruginosa* (MDRP) and has particularly been viewed as a problem in clinical practice. It has been reported that once MDRP is separated in clinical practice, the same strain spreads in the same sickbed or hospital. This is because *Pseudomonas aeruginosa* is strongly viable in the natural environment and can survive in waterworks, toilets, or anywhere else water is used. Thus, even patients or medical personnel originally carrying no MDRP unintentionally carry MDRP from human carriers or living environments, possibly resulting in wide spread of the bacteria. When these carriers suffer from opportunistic infections, there may not exist an antimicrobial drug that exhibits effectiveness from the beginning. Thus, the early detection and containment of this MDRP are highly valued in clinical practice.

Metallo-β-lactamase (MBL) has been reported as one of mechanisms underlying the resistance of MDRP to carbapenem. It has been reported that carbapenem is stable for usual β-lactamase, but unstable for MBL having zinc at the active center. MBL is capable of degrading not only carbapenem but also many β-lactam agents. Many β-lactam agents are often ineffective for MBL-producing bacteria. Among MBLs, particularly, a currently controversial enzyme is plasmid-mediated MBL. The plasmid-mediated MBL was reported in Japan for the first time. However, many cases of this plasmid-mediated MBL have been reported so far not only in Japan but also in Asian and European countries. The resistance to β-lactam agents caused by MBL is now a global concern.

When MBL is present on a cyclic gene called plasmid, bacteria that have acquired this plasmid become MBL-producing bacteria. Such horizontal transmission by the plasmid is performed not only between bacteria of the same species but between bacteria of various species. For example, Enterobacteriaceae carrying this plasmid transmits the plasmid to *Pseudomonas aeruginosa*, which is in turn rendered resistant to β-lactam agents. In other cases, MDRP carrying this plasmid transmits the plasmid to Enterobacteriaceae, possibly resulting in the emergence of new MBL-producing enterobacteria. Thus, any of MBL-producing bacteria have the risk of causing the emergence of new multidrug resistance bacteria. Accordingly, the detection of MBL-producing bacteria is considered as an important issue in medical practice. Moreover, the identification of responsible bacteria is inevitable for the treatment of infections. When the responsible bacteria are multidrug resistance bacteria, the early selection of effective drugs and coping plans is required. In other words, when an infection by MBL-producing bacteria is suspected, early treatment can be achieved in an appropriate manner by conveniently detecting MBL. For these reasons, there has been a demand in medical practice for a method of detecting MBL conveniently, highly selectively, and highly sensitively.

Moreover, these plasmid-mediated MBLs mainly include two types: IMP and VIM types. Depending on the enzyme type, some drugs exhibit sensitivity. Thus, a drug suitable for treatment may be selected rapidly by identifying an IMP or VIM type. Furthermore, MBL inhibitor-containing antimicrobial drugs currently under study or β-lactam agents stable for MBL are considered to differ in inhibitory activity or effectiveness between IMP and VIM MBL-producing bacteria. The identification of the enzyme type is very useful for selection criteria for these drugs developed in the future. Moreover, since the gene sequences of MBL subtypes are common throughout the world, a method of identifying an IMP or VIM type can be used worldwide.

It has been required so far to use specialized machines such as PCR machines for identifying types such as IMP and VIM MBL-producing bacteria. However, simple and rapid identification is preferable for the selection of a drug. Thus, there has been a strong demand for a method of conveniently identifying a type.

Furthermore, if IMP or VIM MBL-producing bacteria can be identified without using specialized machines such as PCR machines, such identification seems to be also useful for various epidemiologic studies or for the preparation of antibiograms in individual facilities in preparation for outbreaks.

The conventional detection of MBL-producing bacteria is described in documents listed below.

Japanese Patent No. 3754993 (the head of the Infectious Disease Surveillance Center) discloses a method of determining whether or not bacteria to be detected are MBL-producing bacteria. Moreover, Japanese Patent Laid-Open Publication No. 2001-299388 (Eiken Chemical Co., Ltd.) and Japanese Patent No. 3964178 (Eiken Chemical Co., Ltd.) disclose a method of testing the drug sensitivity of MBL-producing bacteria by a broth microdilution method using the combination of a liquid medium containing a β-lactam agent and a liquid medium containing a β-lactam agentimetallo-β-lactamase inhibitor. Furthermore, Japanese Patent Laid-Open Publication No. 2004-166694 (SHOWA YAKUHIN KAKO CO., LTD.) discloses a detection method of rapidly identifying β-lactamase and a kit therefor. However, these documents neither disclose nor suggest a method of identifying a type of MBL-producing bacteria or a method of simultaneously performing the detection of MBL-producing bacteria and the identification of a type of the MBL-producing bacteria.

On the other hand, a metallo-β-lactamase inhibitor represented by the formula (I) used in the present invention is a compound disclosed in Japanese Patent No. 4122049. It is known that the compound represented by the formula (I) in combined use with a β-lactam antibiotic strengthens effectiveness for metallo-β-lactamase-producing resistance bacteria in the treatment of bacterial infection.

SUMMARY OF THE INVENTION

The present inventors have found that: metallo-β-lactamase-producing bacteria can be detected by spotting a metallo-β-lactamase inhibitor represented by the formula (I) onto a surface of a solid medium coated with the bacteria to be tested, spotting 3 types of β-lactam agents at 3 respective positions different from the spot of the metallo-β-lactamase inhibitor, culturing the solid medium, and then determining the shape of an inhibition zone formed around the spot of each of the β-lactam agents; and an IMP or VIM type of the metallo-β-lactamase-producing bacteria can also be identified by these procedures. The present invention is based on these findings.

An object of the present invention is to provide a method of identifying metallo-β-lactamase-producing bacteria, particularly, a method of conveniently identifying a type of metallo-β-lactamase-producing bacteria. Another object of the present invention is to provide a kit for use in the identification of metallo-β-lactamase-producing bacteria and an identification method using the kit.

According to the present invention, there is provided a method of identifying metallo-β-lactamase-producing bacteria, comprising spotting metallo-β-lactamase inhibitor represented by the following formula (I) onto a surface of a solid medium coated with the bacteria to be tested, further spotting at least 3 or more β-lactam agents differing in sensitivity to metallo-β-lactamase, at positions different from the spot of the metallo-β-lactamase inhibitor, culturing the solid medium, and then identifying the metallo-β-lactamase-producing bacteria based on the shape of an inhibition zone formed around the spot of each of the β-lactam agents:

[Formula 1]

(I)

wherein

R$^1$ represents a C$_{2-6}$ alkyl group, a C$_{3-7}$ cyclic alkyl group, a hydroxymethyl group, a —C$_{1-3}$ alkylene-phenyl group, a —C$_{0-1}$ alkylene-heterocyclic ring, a —O—C$_{1-6}$ alkyl group, or a —S—C$_{1-6}$ alkyl group, and all of these groups may have a substituent;

R$^2$ represents a C$_{1-6}$ alkyl group, a C$_{3-7}$ cyclic alkyl group, a hydroxymethyl group, a —C$_{1-3}$ alkylene-phenyl group, a —C$_{0-1}$ alkylene-heterocyclic ring, a —O—C$_{1-6}$ alkyl group, or a —S—C$_{1-6}$ alkyl group, and all of these groups may have a substituent; and two M$^1$, which may be the same or different, represent a hydrogen atom, a pharmaceutically acceptable cation, or a pharmaceutically acceptable group that can be hydrolyzed in vivo.

According to the present invention, there is provided a method of identifying a type of metallo-β-lactamase-producing bacteria to be tested, comprising spotting a metallo-β-lactamase inhibitor represented by the following formula (I) onto a surface of a solid medium coated with the bacteria to be tested, further spotting at least 3 or more β-lactam agents differing in sensitivity to metallo-β-lactamase, at positions different from the spot of the metallo-β-lactamase inhibitor, culturing the solid medium, and then identifying the type of the metallo-β-lactamase-producing bacteria to be tested based on the shape of an inhibition zone formed around the spot of each of the β-lactam agents:

[Formula 2]

(I)

wherein

R$^1$ represents a C$_{2-6}$ alkyl group, a C$_{3-7}$ cyclic alkyl group, a hydroxymethyl group, a —C$_{1-3}$ alkylene-phenyl group, a —C$_{0-1}$ alkylene-heterocyclic ring, a —O—C$_{1-6}$ alkyl group, or a —S—C$_{1-6}$ alkyl group, and all of these groups may have a substituent;

R$^2$ represents a C$_{1-6}$ alkyl group, a C$_{3-7}$ cyclic alkyl group, a hydroxymethyl group, a —C$_{1-3}$ alkylene-phenyl group, a —C$_{0-1}$ alkylene-heterocyclic ring, a —O—C$_{1-6}$ alkyl group, or a —S—C$_{1-6}$ alkyl group, and all of these groups may have a substituent; and two M$^1$, which may be the same or different, represent a hydrogen atom, a pharmaceutically acceptable cation, or a pharmaceutically acceptable group that can be hydrolyzed in vivo.

According to the present invention, there is provided a kit for use in the identification of metallo-β-lactamase-producing bacteria, comprising: a substrate having three strips extended in different directions; a disk containing a metallo-β-lactamase inhibitor represented by the following formula (I), the disk being disposed at the center of the substrate; and three disks respectively containing (A) a β-lactam agent that is easily influenced by IMP metallo-β-lactamase but is not easily influenced by VIM metallo-β-lactamase, (B) a β-lactam agent that is easily influenced by both IMP metallo-β-lactamase and VIM metallo-β-lactamase, and (C) a cephem β-lactam agent that is easily influenced by IMP metallo-β-lactamase but is not easily influenced by VIM metallo-β-lactamase, the three disks being disposed on the three respective strips of the substrate such that the distances from the disks of the β-lactam agents to the disk of the metallo-β-lactamase inhibitor are equal:

[Formula 3]

(I)

wherein

R$^1$ represents a C$_{2-6}$ alkyl group, a C$_{3-7}$ cyclic alkyl group, a hydroxymethyl group, a —C$_{1-3}$ alkylene-phenyl group, a —C$_{0-1}$ alkylene-heterocyclic ring, a —O—C$_{1-6}$ alkyl group, or a —S—C$_{1-6}$ alkyl group, and all of these groups may have a substituent;

R$^2$ represents a C$_{1-6}$ alkyl group, a C$_{3-7}$ cyclic alkyl group, a hydroxymethyl group, a —C$_{1-3}$ alkylene-phenyl group, a —C$_{0-1}$ alkylene-heterocyclic ring, a —O—C$_{1-6}$ alkyl group, or a —S—C$_{1-6}$ alkyl group, and all of these groups may have a substituent; and two M$^1$, which may be the same or different, represent a hydrogen atom, a pharmaceutically acceptable cation, or a pharmaceutically acceptable group that can be hydrolyzed in vivo.

According to the present invention, there is provided a method of identifying metallo-β-lactamase-producing bacteria, comprising placing the kit for use in the identification of metallo-β-lactamase-producing bacteria according to the present invention onto a surface of a solid medium coated with the bacteria to be tested, culturing the bacteria, and then identifying the metallo-β-lactamase-producing bacteria based on the shape of an inhibition zone formed around each of the disks of the β-lactam agents.

The present invention also relates to the following (1) to (9):

(1) A method of detecting metallo-β-lactamase-producing bacteria, comprising spotting metallo-β-lactamase inhibitor represented by the following compound (I) onto a surface of a solid medium coated with the bacteria to be tested, further spotting (A) a β-lactam agent that is easily influenced by IMP metallo-β-lactamase but is not easily influenced by VIM metallo-β-lactamase, (B) a β-lactam agent that is easily influenced by both IMP metallo-β-lactamase and VIM metallo-β-lactamase, and (C) a cephem β-lactam agent that is easily influenced by IMP metallo-β-lactamase but is not easily influenced by VIM metallo-β-lactamase, at 3 respective positions different from the spot of the following compound (I), culturing the solid medium, and then identifying the metallo-β-lactamase-producing bacteria based on an inhibition zone formed around the spot of each of the β-lactam agents (A), (B), and (C):

[Formula 4]

(I)

wherein $R^1$ represents a $C_{2-6}$ alkyl group, a $C_{3-7}$ cyclic alkyl group, a hydroxymethyl group, a —$C_{1-3}$ alkylene-phenyl group, a —$C_{0-1}$ alkylene-heterocyclic ring, a —O—$C_{1-6}$ alkyl group, or a —S—$C_{1-6}$ alkyl group, and all of these groups may have a substituent;

$R^2$ represents a $C_{1-6}$ alkyl group, a $C_{3-7}$ cyclic alkyl group, a hydroxymethyl group, a —$C_{1-3}$ alkylene-phenyl group, a —$C_{0-1}$ alkylene-heterocyclic ring, a —O—$C_{1-6}$ alkyl group, or a —S—$C_{1-6}$ alkyl group, and all of these groups may have a substituent; and two $M^1$, which may be the same or different, represent a hydrogen atom, a pharmaceutically acceptable cation, or a pharmaceutically acceptable group that can be hydrolyzed in vivo.

(2) A method of identifying an IMP or VIM type of metallo-β-lactamase-producing bacteria to be tested, comprising spotting a metallo-β-lactamase inhibitor represented by the following compound (I) onto a surface of a solid medium coated with the bacteria to be tested, further spotting (A) a β-lactam agent that is easily influenced by IMP metallo-β-lactamase but is not easily influenced by VIM metallo-β-lactamase, (B) a β-lactam agent that is easily influenced by both IMP metallo-β-lactamase and VIM metallo-β-lactamase, and (C) a cephem β-lactam agent that is easily influenced by IMP metallo-β-lactamase but is not easily influenced by VIM metallo-β-lactamase, at 3 respective positions different from the spot of the following compound (I), culturing the solid medium, and then identifying the IMP or VIM type of the metallo-β-lactamase-producing bacteria to be tested based on an inhibition zone formed around the spot of each of the β-lactam agents (A), (B), and (C):

[Formula 5]

(I)

wherein $R^1$ represents a $C_{2-6}$ alkyl group, a $C_{3-7}$ cyclic alkyl group, a hydroxymethyl group, a —$C_{1-3}$ alkylene-phenyl group, a —$C_{0-1}$ alkylene-heterocyclic ring, a —O—$C_{1-6}$ alkyl group, or a —S—$C_{1-6}$ alkyl group, and all of these groups may have a substituent;

$R^2$ represents a $C_{1-6}$ alkyl group, a $C_{3-7}$ cyclic alkyl group, a hydroxymethyl group, a —$C_{1-3}$ alkylene-phenyl group, a —$C_{0-1}$ alkylene-heterocyclic ring, a —O—$C_{1-6}$ alkyl group, or a —S—$C_{1-6}$ alkyl group, and all of these groups may have a substituent; and two $M^1$, which may be the same or different, represent a hydrogen atom, a pharmaceutically acceptable cation, or a pharmaceutically acceptable group that can be hydrolyzed in vivo.

(3) The method according to (1) or (2), wherein the β-lactam agent (A) is biapenem or doripenem, the β-lactam agent (B) is imipenem or meropenem, and the β-lactam agent (C) is ceftazidime or cefepime.

(4) The method according to (1) or (2), wherein the spots of the β-lactam agents (A), (B), and (C) are fixed at an equal distance from the spot of the compound (I).

(5) The method according to (1) or (2), wherein the identification is performed based on the minimum and maximum values of the inhibition zone formed around each of the β-lactam agents (A), (B), and (C) after culture and the degree of change in radius determined from both the values.

(6) The method according to (1) or (2), wherein in the compound (I), $R^1$ and $R^2$ respectively represent a $C_{2-4}$ alkyl group.

(7) The method according to (6), wherein in the compound (I), $R^1$ and $R^2$ respectively represent an ethyl group, and $M^1$ is a sodium cation or a potassium cation.

(8) A kit for use in the detection of metallo-β-lactamase-producing bacteria, comprising: a substrate having three strips extended in different directions; a disk containing a metallo-β-lactamase inhibitor represented by the compound (I), the disk being disposed at the center of the substrate; and three disks respectively containing (A) a β-lactam agent that is easily influenced by IMP metallo-β-lactamase but is not easily influenced by VIM metallo-β-lactamase, (B) a β-lactam agent that is easily influenced by both IMP metallo-β-lactamase and VIM metallo-β-lactamase, and (C) a cephem β-lactam agent that is easily influenced by IMP metallo-β-lactamase but is not easily influenced by VIM metallo-β-lactamase, the three disks being disposed on the three respective strips of the substrate at an equal distance from the disk of the compound (I).

(9) A method of detecting metallo-β-lactamase-producing bacteria, comprising placing a kit according to (8) onto a surface of a solid medium coated with the bacteria to be tested, culturing the bacteria, and then identifying the metallo-β-lactamase-producing bacteria based on the minimum and maximum values of the inhibition zone formed around each of the disks of the β-lactam agents (A) to (C) and the degree of change in radius determined from both the values.

As described above, among MBLs, a plasmid-mediated enzyme, which is currently controversial MBL, mainly includes two types: IMP and VIM types. Since some drugs exhibit sensitivity depending on the types of these enzymes, it has been desired to rapidly select drugs suitable for treatment by identifying an IMP or VIM type of MBL-producing bacteria to be tested.

According to the identification method of the present invention, MBL-producing bacteria can be detected by a convenient method without using specialized machines such as PCR machines. Furthermore, either an IMP or VIM type of the detected MBL-producing bacteria can also be identified. Thus, drugs suitable for treatment can be selected rapidly. By extension, the administration of ineffective drugs can be prevented, probably leading to reduction in physical or mental burdens to patients and in medical expenses.

Moreover, MBL inhibitor-containing antimicrobial drugs currently under study or β-lactam agents stable for MBL differ in inhibitory activity or effectiveness between IMP and VIM MBL-producing bacteria in some cases. The identification method of the present invention is very useful for selection criteria for these drugs developed in the future.

Furthermore, the identification method of the present invention is also very useful for various epidemiologic studies or for the preparation of antibiograms in individual facilities in preparation for outbreaks.

DESCRIPTION OF EMBODIMENTS

According to a method according to the present invention, whether or not bacteria to be tested are MBL-producing bacteria, and, further, an IMP or VIM type or any other type of the identified MBL-producing bacteria can be determined based on the shape of an inhibition zone formed on a solid medium.

Specifically, the method according to the present invention can be carried out by coating a surface of a solid medium with bacteria to be tested, then spotting thereonto a metallo-β-lactamase inhibitor represented by the formula (I), further spotting at least 3 or more β-lactam agents differing in sensitivity to metallo-β-lactamase, at respective positions different from the spot of the metallo-β-lactamase inhibitor, and culturing the solid medium.

A solid medium that adheres to the standard method specified by the Japanese Society of Chemotherapy or the disk diffusion method specified by CLSI can be used in the present invention. Examples thereof include Muller-Hinton agar media (BD Difco). The form of the solid medium is not particularly limited as long as the method according to the present invention can be carried out. For example, a solid medium of approximately 4 mm in thickness can be used.

The coating of a surface of a solid medium with bacteria to be tested can be performed by a method that adheres to the standard method specified by the Japanese Society of Chemotherapy or the disk diffusion method specified by CLSI. For example, the coating with the bacteria can be performed by uniformly smearing a bacterial solution adjusted to McFarland standard turbidity of 0.5 over the surface of the solid medium using a sterile swab or the like.

A metallo-β-lactamase inhibitor represented by the formula (I) and at least 3 or more β-lactam agents differing in sensitivity to metallo-β-lactamase can be spotted onto the surface of the solid medium coated with the bacteria to be tested.

Examples of the metallo-β-lactamase inhibitor used in the present invention include compounds represented by the following formula (I):

[Formula 6]

wherein $R^1$ represents a $C_{2-6}$ alkyl group, a $C_{3-7}$ cyclic alkyl group, a hydroxymethyl group, a —$C_{1-3}$ alkylene-phenyl group, a —$C_{0-1}$ alkylene-heterocyclic ring, a —O—$C_{1-6}$ alkyl group, or a —S—$C_{1-6}$ alkyl group, and all of these groups may have a substituent;

$R^2$ represents a $C_{1-6}$ alkyl group, a $C_{3-7}$ cyclic alkyl group, a hydroxymethyl group, a —$C_{1-3}$ alkylene-phenyl group, a —$C_{0-1}$ alkylene-heterocyclic ring, a —O—$C_{1-6}$ alkyl group, or a —S—$C_{1-6}$ alkyl group, and all of these groups may have a substituent; and two $M^1$, which may be the same or different, represent a hydrogen atom, a pharmaceutically acceptable cation, or a pharmaceutically acceptable group that can be hydrolyzed in vivo.

In the present specification, the terms "$C_{1-6}$", "$C_{2-6}$", "$C_{3-7}$", "$C_{1-3}$", and "$C_{0-1}$" represent the number of carbon atoms. For example, a "$C_{1-6}$ alkyl group" refers to an alkyl group having 1 to 6 carbon atoms. Moreover, $C_0$ refers to a bond. The term "lower" preferably refers to $C_{1-6}$.

In the present specification, the term "halogen atom" refers to a fluorine, chlorine, bromine, or iodine atom.

In the present specification, the term "heteroatom" refers to a nitrogen, oxygen, or sulfur atom.

In the present specification, the term "alkyl group" or "alkoxy group" as a group or a moiety of a group means a linear or branched alkyl or alkoxy group. Moreover, a lower alkyl group preferably refers to a $C_{1-6}$ alkyl group, which is as defined above.

In the present specification, the term "cyclic alkyl group" as a group or a moiety of a group means a monocyclic alkyl group. Moreover, a lower cycloalkyl group preferably refers to a $C_{3-7}$ cyclic alkyl group, which is as defined above.

In the present specification, preferable examples of the term "heterocyclic ring" include 5- to 14-membered monocyclic to tricyclic heterocyclic rings containing 1 to 4 heteroatoms selected from nitrogen, oxygen, and sulfur atoms, more preferably 5- to 10-membered monocyclic or bicyclic heterocyclic rings containing 1 to 4 heteroatoms selected from nitrogen, oxygen, and sulfur atoms. Preferable specific examples thereof include tetrahydrofuran, furan, pyrrolidine, piperidine, pyrazolidine, imidazolidine, piperazine, morpholine, thiomorpholine, pyrrole, thiophene, oxazole, isoxazole, thiazole, isothiazole, imidazole, pyrazole, pyridine, pyridazine, pyrimidine, pyrazine, triazole, tetrazole, thiadiazole, azetidine, thiazoline, quinuclidine, triazine, isobenzofuran, indole, indolizine, chromene, quinoline, isoquinoline, cinnoline, quinazoline, quinoxaline, phthalazine, purine, and pteridine.

In the present specification, the term "aryl" preferably refers to an aromatic ring such as phenyl or substituted phenyl and a condensed ring such as naphthyl, phenanthrenyl, fluorenyl, or anthryl. The aryl group is preferably phenyl, naphthyl, and fluorenyl groups.

In the present specification, the phrase "may have a substituent" means that the group may have preferably 1 to 6, more preferably 1 to 3 substituents. In this context, the "substituent" is a hydroxy group, a thiol group, a, $C_{1-6}$ alkyl group, a $C_{1-6}$ alkoxy group, an S—$C_{1-6}$ alkyl group, an amino group, a mono-substituted amino group, a di-substituted amino group, an amide group, a guanidyl group, an N-substituted amide group, an N,N-di-substituted amide group, a halogen atom, a carboxyl group, a phenyl group, a substituted phenyl group, a $C_{1-6}$ alkylcarbonyl group, a heterocyclic ring, a heterocyclic carbonyl group, or the like. The phenyl may be condensed with another ring. Preferable examples of the substituent include a hydroxy group, a $C_{1-6}$ alkyl group, a $C_{1-6}$ alkoxy group, an amino group, a mono-substituted amino group, a di-substituted amino group, an amide group, a guanidyl group, an N-substituted amide group, an N,N-di-substituted amide group, a halogen atom, a carboxyl group, a phenyl group (the phenyl may be condensed with another ring), a substituted phenyl group, a $C_{1-6}$ alkylcarbonyl group, a heterocyclic ring, and a heterocyclic carbonyl group.

The alkyl and alkoxy groups as a moiety of a group in the "substituent" such as the $C_{1-6}$ alkyl, $C_{1-6}$ alkoxy, S—$C_{1-6}$ alkyl, and $C_{1-6}$ alkylcarbonyl groups are as defined above. Moreover, the halogen atom is also as defined above. These $C_{1-6}$ alkyl, $C_{1-6}$ alkoxy, S—$C_{1-6}$ alkyl, and $C_{1-6}$ alkylcarbonyl groups may further be substituted by the "substituent" exemplified above. Particularly, the $C_{1-6}$ alkyl and $C_{1-6}$ alkoxy groups may be substituted by a hydroxy group, an amino group, a mono-substituted amino group, a di-substituted amino group, an amide group, a guanidyl group, an N-substituted amide group, an N,N-di-substituted amide group, a carboxyl group, a heterocyclic ring, a phenyl group, a substituted phenyl group, or the like.

When the "substituent" has a carboxyl group or a carboxyl group as a moiety of a group, this carboxyl group may be a pharmaceutically acceptable cation or a pharmaceutically acceptable group that can be hydrolyzed in vivo, and is preferably, for example, sodium salt or potassium salt.

The term "substituted" in the "substituent" such as the mono-substituted amino, di-substituted amino, amide, N-substituted amide, N,N-di-substituted amide, and substituted phenyl groups means that the group preferably has the "substituent" exemplified above.

The heterocyclic ring in the heterocyclic ring and the heterocyclic carbonyl group as the "substituent" is as defined in the "heterocyclic ring" exemplified above.

Preferable examples of the heterocyclic carbonyl include morpholylcarbonyl, piperazylcarbonyl, and piperidylcarbonyl, preferably morpholyl-4-yl-carbonyl, piperazin-4-ylcarbonyl, and (4-hydroxypiperazin)-1-ylcarbonyl.

The "$C_{2-6}$ alkyl group" represented by $R^1$ may be linear or branched. Examples thereof include ethyl, n-propyl, i-propyl, n-butyl, i-butyl, s-butyl, t-butyl, n-pentyl, neopentyl, i-pentyl, t-pentyl, n-hexyl, and i-hexyl groups. The $C_{2-6}$ alkyl group is preferably a $C_{2-4}$ alkyl group, more preferably an ethyl group. This alkyl group may be substituted. Examples of the substituent include the "substituent" exemplified above, more preferably a hydroxy group, a thiol group, an amino group, and a halogen atom.

The "$C_{1-6}$ alkyl group" represented by $R^2$ may be linear or branched. Examples thereof include methyl, ethyl, n-propyl, i-propyl, n-butyl, i-butyl, s-butyl, t-butyl, n-pentyl, neopentyl, i-pentyl, t-pentyl, n-hexyl, and i-hexyl groups. The $C_{1-6}$ alkyl group is preferably a $C_{2-4}$ alkyl group, more preferably an ethyl group. This alkyl group may be substituted. Examples of the substituent include the "substituent" exemplified above, more preferably a thiol group, an amino group, and a halogen atom.

Preferable examples of the "$C_{3-7}$ cyclic alkyl group" represented by $R^1$ or $R^2$ include cyclopropyl, cyclobutyl, cyclopentyl, cyclohexyl, and cycloheptyl groups, more preferably cyclopentyl, cyclohexyl, and cycloheptyl groups. This $C_{3-7}$ cyclic alkyl group may be substituted. Examples of the substituent include the "substituent" exemplified above, more preferably a hydroxy group, a thiol group, a $C_{1-6}$ alkyl group, an amino group, and a halogen atom. Moreover, this $C_{3-7}$ cyclic alkyl group may be condensed with another ring, for example, aryl, preferably phenyl.

Examples of the "—$C_{1-3}$ alkylene-phenyl group" represented by $R^1$ or $R^2$ include benzyl, phenethyl, and phenylpropyl groups. The phenyl group in the —$C_{1-3}$ alkylene-phenyl group may be substituted. Examples of the substituent include the "substituent" exemplified above, more preferably a hydroxy group, a $C_{1-6}$ alkyl group, —COOM (wherein M represents a hydrogen atom or a pharmaceutically acceptable cation), —CO—NR$^{22}$R$^{23}$ (wherein R$^{22}$ and R$^{23}$, which may be the same or different, represent a hydrogen atom or a $C_{1-6}$ alkyl group (preferably a $C_{1-4}$ alkyl group, more preferably a $C_{1-2}$ alkyl group) (this alkyl group may further be substituted by an aminocarbonyl group) or R$^{22}$ and R$^{23}$, together with the nitrogen atom bonded thereto, may represent a 5- or 6-membered saturated heterocyclic ring comprising 1 to 2 oxygen or nitrogen atoms (which preferably refers to a morphonyl group, a piperazyl group, or a piperidyl group) (this heterocyclic ring, particularly, the piperidyl group, may be substituted by a hydroxy group or a $C_{1-6}$ alkanoyloxy group)), —O—R$^{24}$ (wherein R$^{24}$ represents a $C_{1-6}$ alkyl group (preferably a $C_{1-4}$ alkyl group) (this alkyl group may be substituted, and the substituent refers to —COOM (wherein M represents a hydrogen atom, a $C_{1-6}$ alkyl group, or a pharmaceutically acceptable cation), an aminocarbonyl group, an amino group, a guanidino group, or a 5- or 6-membered unsaturated heterocyclic ring comprising 1 to 2 nitrogen atoms (preferably imidazole)), or a 5- or 6-membered saturated heterocyclic ring comprising 1 to 2 nitrogen atoms (preferably pyrrolidine)), and a hydroxymethyl group.

The "—$C_{0-1}$ alkylene-heterocyclic ring" represented by $R^1$ or $R^2$ refers to a -bond-heterocyclic ring or a -methylene-heterocyclic ring. The "heterocyclic ring" is as defined above, and preferable examples thereof include 5- to 10-membered monocyclic or bicyclic heterocyclic rings containing 1 to 4 heteroatoms selected from nitrogen, oxygen, and sulfur atoms, more preferably 5- to 6-membered saturated or unsaturated heterocyclic rings comprising one nitrogen or oxygen atom. Specific examples of the "heterocyclic ring" include tetrahydrofuran, furan, pyrrolidine, piperidine, pyrazolidine, imidazolidine, piperazine, morpholine, thiomorpholine, pyrrole, thiophene, oxazole, isoxazole, thiazole, isothiazole, imidazole, pyrazole, pyridine, pyridazine, pyrimidine, pyrazine, triazole, tetrazole, thiadiazole, azetidine, thiazoline, quinuclidine, triazine, isobenzofuran, indole, indolizine, chromene, quinoline, isoquinoline, cinnoline, quinazoline, quinoxaline, phthalazine, purine, and pteridine. The bond or the methylene group may be bonded to any position on the heterocyclic ring. One or more hydrogen atoms on this heterocyclic ring on the —$C_{0-1}$ alkylene-heterocyclic ring may be substituted. Examples of the substituent include the "substituent" exemplified above, more preferably a hydroxy group, a thiol group, a $C_{1-6}$ alkyl group, an amino group, and a halogen atom.

The "—O—$C_{1-6}$ alkyl group" represented by $R^1$ or $R^2$ is a $C_{1-6}$ alkoxy group which may be linear, branched, or cyclic, preferably a —O—$C_{1-4}$ alkyl group. Examples thereof include methoxy, ethoxy, propoxy, isopropoxy, butoxy, isobutoxy, s-butoxy, and t-butoxy, more preferably methoxy, ethoxy, propoxy, isopropoxy, and t-butoxy. The alkyl moiety in this group may be substituted. Examples of the substituent include the "substituent" exemplified above, more preferably a hydroxy group, a thiol group, a $C_{1-6}$ alkyl group, an amino group, a halogen atom, and a phenyl group.

The "—S—$C_{1-6}$ alkyl group" represented by $R^1$ or $R^2$ is a $C_{1-6}$ alkylthio group which may be linear, branched, or cyclic, preferably a —S—$C_{1-4}$ alkyl group. Examples thereof include methylthio, ethylthio, propylthio, isopropylthio, butylthio, isobutylthio, s-butylthio, and t-butylthio, more preferably methylthio, ethylthio, propylthio, isopropylthio, and t-butylthio. The alkyl moiety in this group may be substituted. Examples of the substituent include the "substituent" exemplified above, more preferably a hydroxy group, a thiol group, a $C_{1-6}$ alkyl group, an amino group, a halogen atom, and a phenyl group.

The "pharmaceutically acceptable cation" represented by $M^1$ is a cation that is capable of forming a salt with either or both of the carboxyl groups in the formula (I). Examples thereof include alkali metals, alkaline-earth metals, ammonium, and organic bases, preferably lithium, sodium, potassium, magnesium, calcium, ammonium, ethanolamine, triethanolamine, trimethylamine, triethylamine, and diisopropylamine.

The "pharmaceutically acceptable group that can be hydrolyzed in vivo" represented by $M^1$ refers to an eliminable group that is bonded to either or both of the carboxyl groups in the formula (I) and also refers to a group that is hydrolyzed and eliminated in vivo through metabolism to form a carboxyl group. The "pharmaceutically acceptable group that can be hydrolyzed in vivo" is preferably an ester residue. Examples thereof include those routinely used, such as a lower alkyl group, a lower alkenyl group, a lower alkylcarbonyloxy-lower alkyl group, a lower cycloalkylcarbonyloxy-lower alkyl group, a lower cycloalkylmethylcarbonyloxy-lower alkyl group, a lower alkenylcarbonyloxy-lower alkyl group, an arylcarbonyloxy-lower alkyl group, a tetrahydrofuranylcarbonyloxymethyl group, a lower alkoxy-lower alkyl group, a lower alkoxy-lower alkoxy-lower alkyl group, an arylmethyloxy-lower alkyl group, an arylmethyloxy-lower alkoxy-lower alkyl group, a lower alkoxycarbonyloxy-lower alkyl group, a lower alkoxycarbonyloxy-lower alkoxy group, a lower cycloalkoxycarbonyloxy-lower alkyl group, a lower cycloalkylmethoxycarbonyloxy-lower alkyl group, an aryloxycarbonyloxy-lower alkyl group, a 3-phthalidyl group which may have a substituent on the aromatic ring, a 2-(3-phthalidylidene)ethyl group which may have a substituent on the aromatic ring, a 2-oxotetrahydrofuran-5-yl group, a mono-lower alkylaminocarbonyloxymethyl group, a di-lower alkylaminocarbonyloxymethyl group, a 2-oxo-5-lower alkyl-1,3-dioxolen-4-ylmethyl group, a piperidinyl carbonyloxy-lower alkyl group which may have a substituent, and a lower alkyl-lower cycloalkylaminocarbonyloxy-lower alkyl group.

The "pharmaceutically acceptable group that can be hydrolyzed in vivo" is preferably, for example, methyl, ethyl, 1-(cyclohexyloxycarbonyloxy)ethyl, acetoxymethyl, 1-(isopropyloxycarbonyloxy)ethyl, 1-(ethoxycarbonyloxy)ethyl, pivaloyloxymethyl, cyclohexyloxycarbonyloxymethyl, 1-(isobutyloxycarbonyloxy)ethyl, 1-(cyclohexyloxycarbonyloxy)-2-methylpropan-1-yl, isobutyloxycarbonyloxymethyl, isopropyloxycarbonyloxymethyl, isobutyryloxymethyl, (pentan-1-yl)oxycarbonyloxymethyl, (butan-1-yl)oxycarbonyloxymethyl, (1-ethyl propan-1-yl)oxycarbonyloxymethyl, isopentyloxycarbonyloxymethyl, (propan-1-yl)oxymethyl, ethoxycarbonyloxymethyl, neopentyloxycarbonyloxymethyl, methoxycarbonyloxymethyl, cyclopentyloxycarbonyloxymethyl, t-butoxycarbonyloxymethyl, phthalidyl, 1-(methoxycarbonyloxy)ethyl, 1-(cyclopentyloxycarbonyloxy)ethyl, (tetrahydropyran-4-yl)oxycarbonyloxymethyl, 1-(neopentyloxycarbonyloxy)ethyl, (piperidin-1-yl)carbonyloxymethyl, allyl, 1-(t-butoxycarbonyloxy)ethyl, (N,N-di-n-propylamino)carbonyloxymethyl, phenyloxycarbonyloxymethyl, (5-methyl-2-oxo-1,3-dioxolen-4-yl)methyl, (cis-2,6-dimethylpiperidin-1-yl)carbonyloxymethyl, N,N-di-(butan-1-yl)aminocarbonyloxymethyl, hexan-1-yl, N-(hexan-1-yl)-N-methylaminocarbonyloxymethyl, N,N-diisobutylaminocarbonyloxymethyl, N,N-diisopropylaminocarbonyloxymethyl, N-cyclohexyl-N-methylaminocarbonyloxymethyl, N-pentan-1-ylaminocarbonyloxymethyl, N-cyclohexyl-N-ethylaminocarbonyloxymethyl, N-isobutyl-N-isopropylaminocarbonyloxymethyl, N-t-butyl-N-ethylaminocarbonyloxymethyl, 1-[(cis-2,6-dimethylpiperidin-1-yl)carbonyloxy]ethyl, 1-(N,N-diisopropylaminocarbonyloxy)ethyl, and N-ethyl-N-isoamylaminocarbonyloxymethyl groups.

In the formula (I), $R^1$ is preferably a $C_{2-6}$ alkyl group or a $C_{3-7}$ cyclic alkyl group, more preferably a $C_{2-4}$ alkyl group, even more preferably an ethyl group.

In the formula (I), $R^2$ is preferably a $C_{1-6}$ alkyl group or a $C_{3-7}$ cyclic alkyl group, more preferably a $C_{2-4}$ alkyl group, even more preferably an ethyl group.

In the formula (I), two $M^1$, which may be the same or different, are preferably a hydrogen atom or a pharmaceutically acceptable cation, more preferably a sodium cation or a potassium cation.

In a preferable aspect, the metallo-β-lactamase inhibitor used in the present invention is a compound of the formula (I) wherein $R^1$ is a $C_{2-6}$ alkyl group or a $C_{3-7}$ cyclic alkyl group; $R^2$ is a $C_{1-6}$ alkyl group or a $C_{3-7}$ cyclic alkyl group; and two $M^1$, which may be the same or different, are a hydrogen atom or a pharmaceutically acceptable cation.

In a more preferable aspect, the metallo-β-lactamase inhibitor used in the present invention is a compound of the formula (I) wherein $R^1$ is a $C_{2-4}$ alkyl group; $R^2$ is a $C_{2-4}$ alkyl group; and two $M^1$ are a sodium cation or a potassium cation.

In an even more preferable aspect, the metallo-β-lactamase inhibitor used in the present invention is a compound of the formula (I) wherein $R^1$ is an ethyl group; $R^2$ is an ethyl group; and two $M^1$ are a sodium cation or a potassium cation.

The compound of the formula (I) can be produced according to the description of Japanese Patent No. 41222049.

Examples of the "at least 3 or more β-lactam agents differing in sensitivity to metallo-β-lactamase" used in the present invention include: a β-lactam agent that is easily influenced by IMP metallo-β-lactamase but is not easily influenced by VIM metallo-β-lactamase; a β-lactam agent that is easily influenced by both IMP metallo-β-lactamase and VIM metallo-β-lactamase; a cephem β-lactam agent that is easily influenced by IMP metallo-β-lactamase but is not easily influenced by VIM metallo-β-lactamase; and a β-lactam agent that is easily influenced by VIM metallo-β-lactamase but is not easily influenced by IMP metallo-β-lactamase.

The at least 3 or more β-lactam agents differing in sensitivity to metallo-β-lactamase preferably comprise at least a cephem β-lactam agent that is easily influenced by IMP metallo-β-lactamase but is not easily influenced by VIM metallo-β-lactamase and more preferably comprise at least: a β-lactam agent that is easily influenced by IMP metallo-β-lactamase but is not easily influenced by VIM metallo-β-lactamase; a β-lactam agent that is easily influenced by both IMP metallo-β-lactamase and VIM metallo-β-lactamase; and a cephem β-lactam agent that is easily influenced by IMP metallo-β-lactamase but is not easily influenced by VIM metallo-β-lactamase.

The antibacterial powers of the β-lactam agents decrease by the production of metallo-β-lactamase. However, the degree of this decrease varies depending on the type of metallo-β-lactamase or the types of the β-lactam agents. As a result, the degree of formation of an inhibition zone (i.e., the shape of an inhibition zone) derived from each β-lactam agent also differs depending on the type of metallo-β-lactamase.

In the present specification, the "β-lactam agent that is easily influenced by metallo-β-lactamase" means a β-lactam agent that forms a smaller inhibition zone in the presence of each metallo-β-lactamase than that in the absence of metallo-β-lactamase.

In the present specification, the "β-lactam agent that is not easily influenced by metallo-β-lactamase" means a β-lactam agent that forms an inhibition zone having a size unchanged or less changed even in the presence of each metallo-β-lactamase.

The level of this influence differs depending on the combination of metallo-β-lactamase and a β-lactam agent. β-lactam agents can be classified according to the purpose. The β-lactam agents can be classified and selected as follows with the level of this influence depending on these types of metallo-β-lactamases as selection criteria.

Examples of the β-lactam agent that is easily influenced by IMP metallo-β-lactamase but is not easily influenced by VIM metallo-β-lactamase (hereinafter, also referred to as a "β-lactam agent (A)") include carbapenem β-lactam agents (e.g., biapenem and doripenem). This β-lactam agent is preferably biapenem.

Examples of the β-lactam agent that is easily influenced by both IMP metallo-β-lactamase and VIM metallo-β-lactamase (hereinafter, also referred to as a "β-lactam agent (B)") include carbapenem β-lactam agents (e.g., imipenem and meropenem). This β-lactam agent is preferably imipenem.

Examples of the cephem β-lactam agent that is easily influenced by IMP metallo-β-lactamase but is not easily influenced by VIM metallo-β-lactamase (hereinafter, also referred to as a "β-lactam agent (C)") include ceftazidime and cefepime. This β-lactam agent is preferably ceftazidime.

Other examples of the β-lactam agents include a β-lactam agent that is easily influenced by VIM metallo-β-lactamase but is not easily influenced by IMP metallo-β-lactamase.

Any β-lactam agent that is included in these classifications may be used, and the present invention is not limited to the β-lactam agents exemplified above.

In the present specification, the term "spotting" means that the drug of interest is disposed at the predetermined position.

The order of spotting is not particularly limited. For example, the metallo-β-lactamase inhibitor is first spotted, and next, the at least 3 or more β-lactam agents differing in sensitivity to metallo-β-lactamase can be spotted.

The metallo-β-lactamase inhibitor and each β-lactam agent can be spotted, for example, in a disk form.

The disk containing the metallo-β-lactamase inhibitor can be prepared using a filter paper of appropriate size and shape. For example, this disk can be prepared by impregnating a ¼-inch round filter paper with the metallo-β-lactamase inhibitor, if necessary using a solvent.

Drug disks respectively containing the β-lactam agents are commercially available, and they can be used as the disks respectively containing the β-lactam agents. Even if corresponding commercially available products are absent, a filter paper of appropriate size and shape (e.g., a ¼-inch round filter paper) impregnated with each of the β-lactam agents, if necessary using a solvent, can be used.

The amounts of the metallo-β-lactamase inhibitor and each β-lactam agent spotted can be determined appropriately with consideration given to the diffusibility or culture time (diffusion time) of each β-lactam agent on the solid medium surface and further to the strength of the inhibitory effect of the metallo-β-lactamase inhibitor on metallo-β-lactamase, etc. For example, for 300 μg of the metallo-β-lactamase inhibitor represented by the formula (I), 100 μg of the β-lactam agent (A), 100 μg of the β-lactam agent (B), and 300 μg of the β-lactam agent (C) can be used to thereby form an inhibition zone appropriate for identification. However, these amounts are given merely as a guideline and can be changed appropriately with consideration given to the shape, size, or the like of an inhibition zone formed around the β-lactam agent according to the type of the bacteria to be tested.

The positions at which the metallo-β-lactamase inhibitor and each β-lactam agent are respectively spotted can be set such that the distances from the disks respectively containing the β-lactam agents to the disk containing the metallo-β-lactamase inhibitor are equal on the same solid medium surface. In this context, the "distance" means the distance from the center of the disk containing the metallo-β-lactamase inhibitor to that of each of the disks respectively containing the β-lactam agents. Preferably, these disks respectively containing the β-lactam agents can be disposed such that they are uniformly spaced on the circumference at an equal distance from the center.

Also, the positions at which the metallo-β-lactamase inhibitor and each β-lactam agent are respectively spotted is preferably set such that the disk containing the metallo-β-lactamase inhibitor is disposed at the center of the solid medium surface and the disks respectively containing the β-lactam agents are respectively disposed at an equal distance from the disk containing the metallo-β-lactamase inhibitor.

For example, when the disk containing the metallo-β-lactamase inhibitor is disposed at the center, the disks respectively containing the β-lactam agents can be disposed such that their centers are respectively positioned at an equal distance, for example, 20 mm, from the center of the disk containing the metallo-β-lactamase inhibitor and they are also uniformly spaced on the circumference at an equal distance from the center.

Moreover, for identification, these β-lactam agents can also be disposed on separate solid media at an equal distance from the disk containing the metallo-β-lactamase inhibitor, without using the same solid medium.

The disks respectively containing the β-lactam agents and the disk containing the metallo-β-lactamase inhibitor are placed onto the surface of the solid medium coated with the bacteria to be tested, and then, the solid medium can be cultured.

Culture conditions that adhere to the standard method specified by the Japanese Society of Chemotherapy or the disk diffusion method specified by CLSI can be used. The culture conditions can be determined appropriately with consideration given to the diffusion range of the β-lactam agents, etc., and can be set to within ranges of, for example, 35 to 37° C. and 12 to 36 hours.

By this culture, each β-lactam agent and the metallo-β-lactamase inhibitor placed on the surface of the solid medium are diffused into the surface and inside of the solid medium. As a result, an inhibition zone is formed around each β-lactam agent. The degree of formation of an inhibition zone (i.e., the shape of an inhibition zone) derived from each β-lactam agent differs depending on whether or not the bacteria to be tested are metallo-β-lactamase-producing bacteria and the type of metallo-β-lactamase produced by the identified metallo-β-lactamase-producing bacteria. Thus, whether or not the bacteria to be tested are MBL-producing bacteria, and, further, an IMP or VIM type or any other type of the identified MBL-producing bacteria can be determined based on the shape of the inhibition zone thus formed.

Hereinafter, the shape of the inhibition zone will be described specifically.

Figure 1:
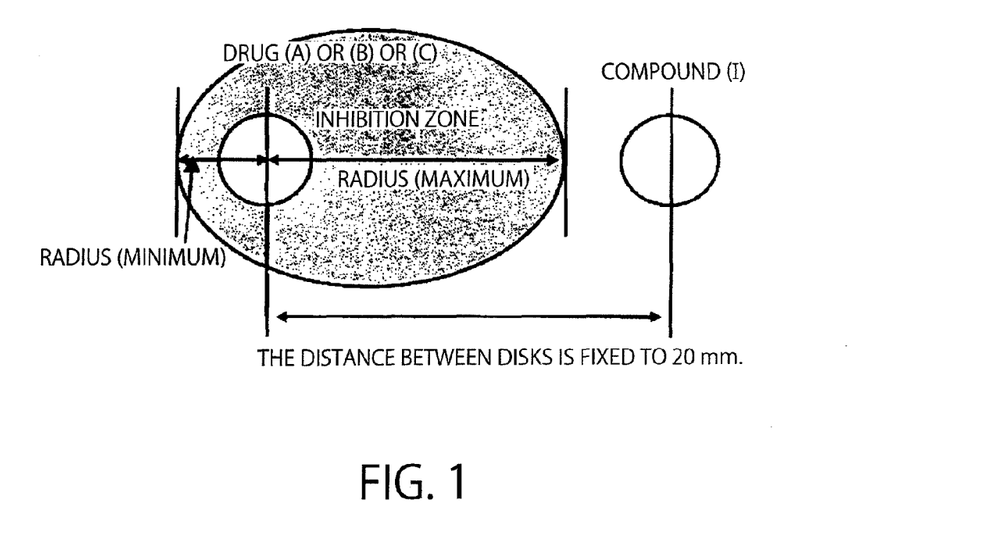
FIG. 1 is a diagram showing measured positions in an inhibition zone.

When the bacteria to be tested are MBL-producing bacteria, the shape of an inhibition zone formed around each β-lactam agent varies depending on the effect of the metallo-β-lactamase inhibitor (compound (I)). In this case, the inhibition zone formed around each β-lactam agent can be divided into two subzones (i.e., an inhibition subzone formed on the side opposite to the compound (I)-containing disk and an inhibition subzone formed on the compound (I)-containing disk side) by measurement along the center lines of the β-lactam agent-containing and compound (I)-containing disks (FIG. 1).

The inhibition subzone formed on the side opposite to the compound (I)-containing disk is not subject to the effect of the metallo-β-lactamase inhibitor. Thus, its radius can be minimized in the whole inhibition zone (e.g., the numerical value obtained here can be defined as "A1", "B1" and "C1" for the β-lactam agents (A), (B) and (C), respectively (Table 1)). When no inhibition zone is formed, the radius of the disk can be used.

Figure 2:
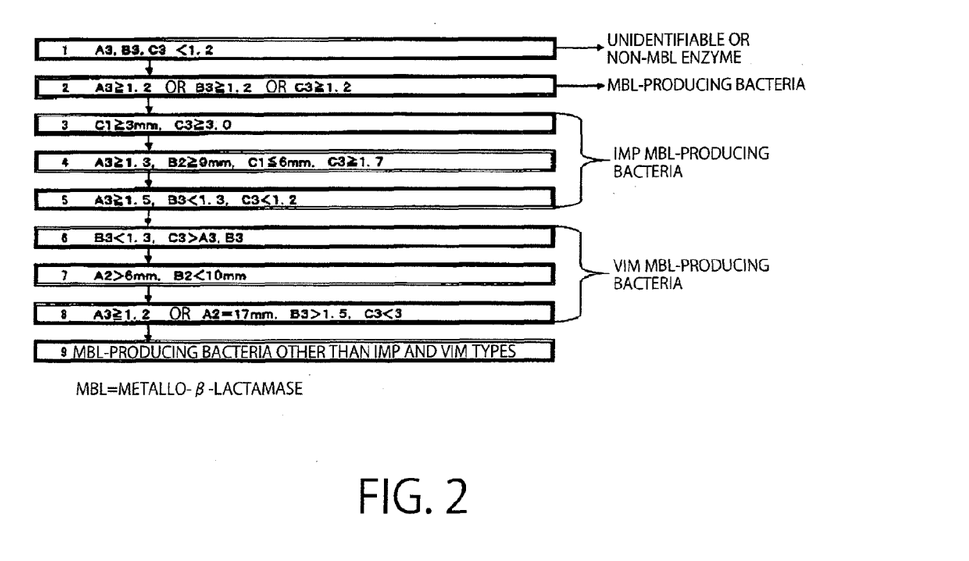
FIG. 2 is a flowchart showing the identification of an MBL type.

The inhibition subzone formed on the compound (I)-containing disk side is subject to the effect of the metallo-β-lactamase inhibitor. Thus, its radius can be maximized in the whole inhibition zone (e.g., the numerical value obtained here can be defined as "A2", "B2" and "C2" for the β-lactam agents (A), (B) and (C), respectively (Table 1)). When no inhibition zone is formed, the radius of the disk can be used. Moreover, when the formed inhibition zone is wider than the distance between the disks, the distance from the center of the drug-containing disk to the compound (I)-containing disk can be used (e.g., "A2" in the flow 8 in the flowchart of FIG. 2 represents the distance from the center of the β-lactam agent (A)-containing disk to the compound (I)-containing disk).

The degree of change in the shape of the inhibition zone caused by the effect of the metallo-β-lactamase inhibitor can be measured as the ratio between the minimum and maximum radiuses of the inhibition zone, i.e., the degree of change in radius. For example, it can be calculated by dividing the maximum radius of the inhibition zone by the minimum radius thereof (e.g., this calculated value can be defined as "A3", "B3", and "C3", respectively (Table 1)).

TABLE 1

| Inhibition zone radius (mm) | | |
| --- | --- | --- |
| Minimum | Maximum | Ratio = Maximum/Minimum |
| A1 | A2 | A3 |
| B1 | B2 | B3 |
| C1 | C2 | C3 |

In the method according to the present invention, the "shape of the inhibition zone" can be determined by at least one value as an index selected from the minimum radius of the inhibition zone, the maximum radius of the inhibition zone, and the ratio between the minimum and maximum radiuses of the inhibition zone (degree of change in radius).

Whether or not the bacteria to be tested are metallo-β-lactamase-producing bacteria can be determined based on whether or not the presence of the metallo-β-lactamase inhibitor influences the size of the inhibition zone, i.e., the degree of change in radius. When the presence of the metallo-β-lactamase inhibitor influences the size of the inhibition zone, i.e., the degree of change in radius becomes equal to or larger than the predetermined size, the bacteria to be tested can be identified as metallo-β-lactamase-producing bacteria.

Whether or not the bacteria to be tested are IMP metallo-β-lactamase-producing bacteria or VIM metallo-β-lactamase-producing bacteria can be determined based on the degree of change in radius in the inhibition zone of each β-lactam agent caused by the presence of the metallo-β-lactamase inhibitor. When the degree of change in radius in the inhibition zone of the β-lactam agent that is easily influenced by IMP metallo-β-lactamase becomes equal to or larger than the predetermined size due to the presence of the metallo-β-lactamase inhibitor, the bacteria to be tested can be identified as IMP metallo-β-lactamase-producing bacteria. When the degree of change in radius in the inhibition zone of the β-lactam agent that is easily influenced by VIM metallo-β-lactamase becomes equal to or larger than the predetermined size due to the presence of the metallo-β-lactamase inhibitor, the bacteria to be tested can be identified as VIM metallo-β-lactamase-producing bacteria. Whether or not the bacteria to be tested are IMP metallo-β-lactamase-producing bacteria or VIM metallo-β-lactamase-producing bacteria can also be determined based on the range of the predetermined minimum or maximum numerical value.

For carrying out the method according to the present invention, a decision flow for determining whether or not the bacteria to be tested are metallo-β-lactamase-producing bacteria and, further, either an IMP or VIM type of the bacteria can be designed using the degree of change in radius and numerical values such as minimum and maximum radiuses (e.g., "A1" to "A3", "B1" to "B3" and "C1" to "C3" in Table 1).

The specific numerical values used in identification differ depending on the solid medium used, the types of the metallo-β-lactamase and β-lactam agents, the radiuses of the disks, or the distance between the disks. Thus, the decision flow can be designed individually according to a protocol for carrying out the method according to the present invention. Metallo-β-lactamase-producing bacteria whose metallo-β-lactamase type has been confirmed can be used for the design of the decision flow.

For example, when the method according to the present invention is carried out according to the protocol of Examples in the present specification, a decision flow shown in FIG. 2 can be used. In the decision flow of FIG. 2, bacteria that correspond to the flow 2 are determined to be MBL-producing bacteria; bacteria that correspond to the flows 3 to 5 can be identified as IMP MBL-producing bacteria; and bacteria that correspond to the flows 6 to 8 without corresponding to the flows 3 to 5 can be identified as VIM MBL-producing bacteria. Bacteria that correspond to the flow 1 can possibly be identified by appropriately diluting a coating solution and conducting the same test again. Bacteria that cannot be identified using the decision flow of FIG. 2 can be determined to be MBL-producing bacteria other than IMP and VIM types or non-MBL-producing bacteria including bacteria producing not MBL but serine-β-lactamase (flow 9).

According to the present invention, there is also provided a kit for use in the identification of metallo-β-lactamase-producing bacteria for carrying out the method according to the present invention. According to the kit according to the present invention, the method according to the present invention can be carried out conveniently.

The kit for use in the identification of metallo-β-lactamase-producing bacteria according to the present invention comprises at least a substrate in a plate form (strip form) on which β-lactam agents (A) to (C) are disposed (preferably, fixed) at an equal distance from a disk containing a compound (I) positioned at the center.

The substrate used in the kit according to the present invention can be a substrate in a thin plate form (strip form) on which β-lactam agents (A) to (C) can be disposed at an equal distance from a disk containing a compound (I) positioned at the center. The substrate is preferably made of a water-unabsorbable material such as a plastic. The substrate can be provided with calibration marks (e.g., at a 0.5-mm interval). The disks used in the kit of the present invention can be the same disks as those described in the method of the present invention.

Figure 3:
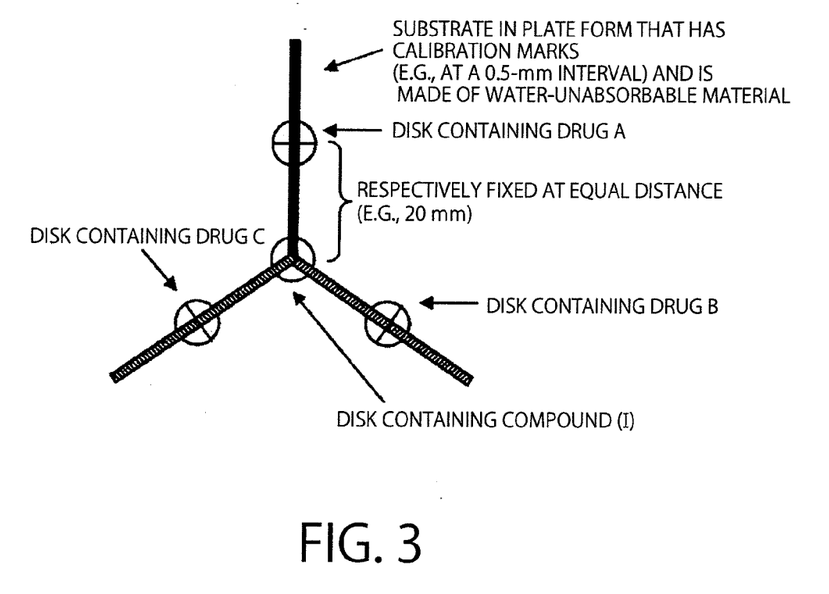
FIG. 3 is a diagram illustrating a kit of the present invention.

One example of the kit according to the present invention is shown in FIG. 3. A substrate has three strips extended in different directions (structure with three branches) for respectively disposing disks at an equal distance from a disk containing a compound (I) positioned at the center. The angle and size of the strips (branched structure) are not particularly limited and can be determined appropriately with consideration given to the size of the solid medium used, etc. The concentration of the drug in each disk can be determined appropriately with consideration given to the same points as those described in the method of the present invention. In this context, the drug names and sizes described in the diagram are described merely for illustration, and the kit of the present invention is not limited to them.

A method of identifying bacteria to be tested using the kit comprises placing the kit with its disk surface downward onto a surface of a solid medium coated with the bacteria to be tested, culturing the solid medium in the same way as in the method to form an inhibition zone, measuring the radius of the inhibition zone by visual observation using the calibration marks on the substrate, and identifying the bacteria to be tested as IMP or VIM MBL-producing bacteria or the other bacteria by using the decision flow. This method can be performed in the same way as in the method of the present invention except that the kit is used.

EXAMPLES

Hereinafter, a test method of the present invention will be further described with reference to Examples.

Example 1

A test shown below was conducted using, as bacteria to be tested, a total of 41 strains of *Pseudomonas aeruginosa* (including *Pseudomonas putida*): IMP types (10 IMP-1-producing bacterial strains, 18 IMP-7-producing bacterial strains, 4 IMP-10-producing bacterial strains, and 2 IMP-β-producing bacterial strains) and VIM types (3 VIM-1-producing bacterial strains and 4 VIM-2-producing bacterial strains). These 41 strains were strains whose MBL type had already been identified by PCR or the like, and this Example was performed using them.

According to the disk diffusion method specified by CLSI, a Muller-Hinton agar medium was coated with a bacterial solution adjusted to McFarland standard turbidity of 0.5. No water droplet of the bacterial solution on the medium surface was confirmed, and round filter papers (diameter: approximately 6 mm) respectively containing 300 μg of a compound (I), 100 μg of biapenem as a drug (A), 100 μg of imipenem as a drug (B), and 300 μg of ceftazidime as a drug (C) were placed thereonto as drug-containing disks. The compound (I) used was a compound represented by the formula (I) wherein both $R^1$ and $R^2$ are an ethyl group, and $M^1$ is a sodium cation (disodium 2,3-diethylmaleate). The compound (I) was placed at the center of the agar medium, while the drugs (A) to (C) were placed such that the center of each disk was 20 mm distant from the center of the compound (I). After overnight culture at 35° C., the minimum and maximum radiuses of a growth inhibition zone around each disk were measured, and the degree of change in radius was calculated according to Table 1. The IMP or VIM MBL-producing bacteria were identified using a decision flow of FIG. 2.

Figure 6:
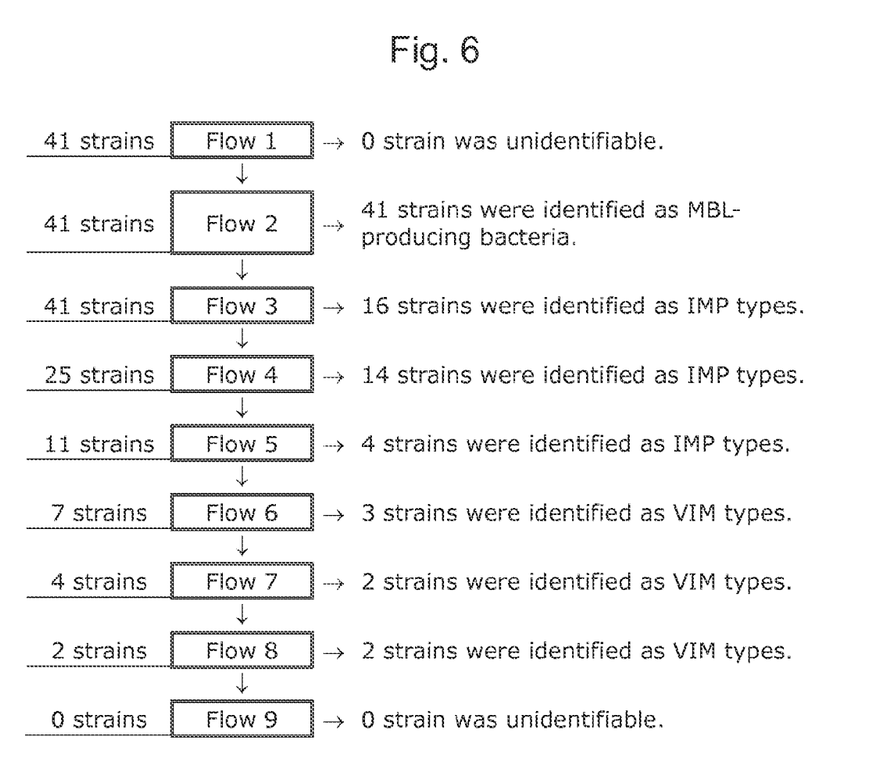
FIG. 6 shows the results of identification of the MBL type of Example 1 using the flowchart in FIG. 2.

The results are shown in FIG. 6.

First, all the 41 strains corresponded to the flow 2 and were thus determined to be MBL-producing bacteria.

Next, 16 out of the 41 strains corresponded to the flow 3 in the decision flow, and all of these were IMP MBL-producing bacteria. Of the remaining 25 strains, 14 corresponded to the flow 4 in the decision flow, and all of these were IMP MBL-producing bacteria. Of the remaining 11 strains, 4 corresponded to the flow 5 in the decision flow, and all of these were IMP MBL-producing bacteria.

Moreover, 3 out of the remaining 7 strains corresponded to the flow 6 in the decision flow, and all of these were VIM MBL-producing bacteria. Of the remaining 4 strains, 2 corresponded to the flow 7 in the decision flow, and all of these were VIM MBL-producing bacteria. Of the remaining 2 strains, 2 corresponded to the flow 8 in the decision flow, and all of these were VIM MBL-producing bacteria.

Thus, it was demonstrated that the results of the decision flow agree with the actual types.

Example 2

Figure 4:
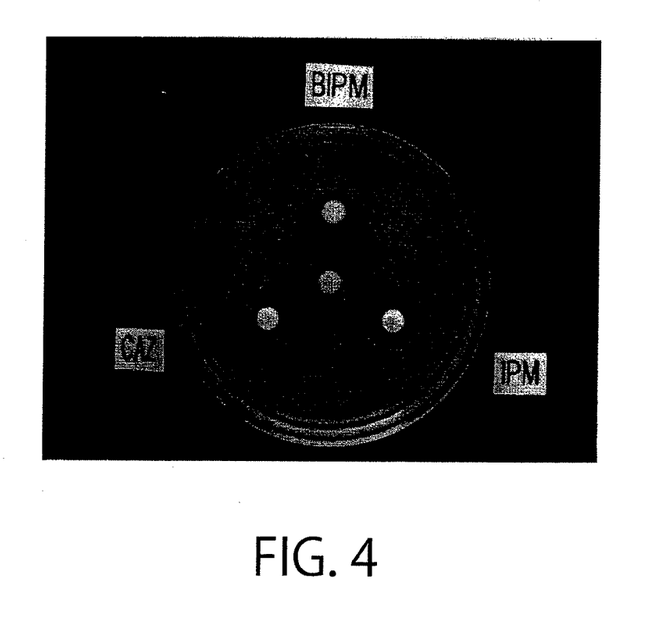
FIG. 4 is a photograph of an inhibition zone on a solid medium obtained in Example 2.

An example of the decision flow of Examples and FIG. 2 will be further described using a photograph of FIG. 4.

In Example 2, bacteria to be tested were IMP-1-producing *Pseudomonas aeruginosa*. According to the disk diffusion method specified by CLSI, a Muller-Hinton agar medium was coated with the *Pseudomonas aeruginosa*, and disks were then placed thereonto. The state after overnight culture at 35° C. is shown in FIG. 4.

In FIG. 4, the upper disk contained biapenem (BIPM) (A); the lower right disk contained imipenem (IPM) (B); the lower left disk contained ceftazidime (CAZ) (C); and the central disk was a compound (I)-containing disk. The compound (I) used was a compound represented by the formula (I) wherein both $R^1$ and $R^2$ are an ethyl group, and $M^1$ is a sodium cation (disodium 2,3-diethylmaleate). Black portions around the disks are inhibition zones. It is observed that the inhibition zone of each β-lactam agent is changed by the presence of the compound (I)-containing disk. An inhibition zone radius positioned on the lateral side in relation to the center of each β-lactam agent-containing disk represents the minimum radius of the inhibition zone, and an inhibition zone radius closer to the center represents the maximum radius of the inhibition zone. In this case, "A1" is 5.5 mm, "B1" is 6.5 mm, and "C1" is 3.5 mm. On the other hand, "A2" is 16.0 mm, "B2" is 14.0 mm, and "C2" is 14.5 mm. From these numerical values, "A3", "B3", and "C3" are calculated to be 2.9, 2.2, and 4.1, respectively. When these numerical values are applied to the decision flow of FIG. 2, "A3", "B3", and "C3" are not less than 1.2 and thus, do not correspond to the flow 1 in the decision flow. However, all of "A3", "B3", and "C3" are 1.2 or more and thus correspond to the flow 2 in the decision flow. Thus, the bacteria to be tested are identified as MBL-producing bacteria. Furthermore, "C1" which is 3 mm or more and "C3" which is 3 or more, correspond to the flow 3 in the decision flow. Thus, the bacteria to be tested were identified as IMP MBL-producing bacteria.

Example 3

Figure 5:
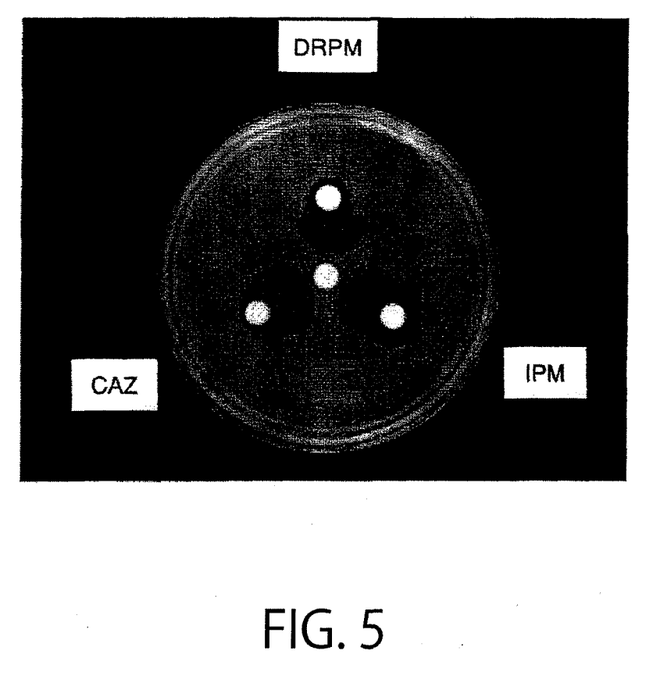
FIG. 5 is a photograph of an inhibition zone on a solid medium obtained in Example 3.

An identification test was conducted using, as bacteria to be tested, a total of 9 strains of *Pseudomonas aeruginosa* (including *Pseudomonas putida*): IMP types (3 IMP-1-producing bacterial strains, 2 IMP-7-producing bacterial strains, and 1 IMP-β-producing bacterial strain) and VIM types (1 VIM-1-producing bacterial strain and 2 VIM-2-producing bacterial strains). 300 μg of a compound (I) wherein both $R^1$ and $R^2$ are an ethyl group, and $M^1$ is a sodium cation (disodium 2,3-diethylmaleate), 100 μg of doripenem (DRPM) as a drug (A), 100 μg of imipenem (IPM) as a drug (B), and 300 μg of ceftazidime (CAZ) as a drug (C) were used to perform culture and inhibition zone measurement in the same way as in Example 1. As a result of determination using the decision flow of FIG. 2, 2 out of the 9 strains corresponded to the flow 3, 4 out thereof corresponded to the flow 4, 1 out thereof corresponded to the flow 6, and 2 out thereof corresponded to the flow 8. All the strains that corresponded to the flows 3 and 4 were IMP MBL-producing bacteria. All the strains that corresponded to the flows 6 and 8 were VIM MBL-producing bacteria. The disks obtained using IMP MBL-producing bacteria are shown in FIG. 5.

The invention claimed is:

1. A method of identifying a metallo-β-lactamase-producing bacteria, comprising:
spotting a metallo-β-lactamase inhibitor represented by the following Formula (1) onto a surface of a solid medium coated with a bacteria to be tested,

[Formula 1]

wherein
$R^1$ represents a $C_{2-6}$ alkyl group, a $C_{3-7}$ cyclic alkyl group, a hydroxymethyl group, a —$C_{1-3}$ alkylene-phenyl group, a —$C_{0-1}$ alkylene-heterocyclic ring, a —O—$C_{1-6}$ alkyl group, or a —S—$C_{1-6}$ alkyl group, and each of these groups may have a substituent $R^2$ represents a $C_{1-6}$ alkyl group, a $C_{3-7}$ cyclic alkyl group, a hydroxymethyl group, a —$C_{1-3}$ alkylene-phenyl group, a —$C_{0-1}$ alkylene-heterocyclic ring, a —O—$C_{1-6}$ alkyl group, or a —S—$C_{1-6}$ alkyl group, and each of these groups may have a substituent; and each $M^1$, which may be the same or different, represent a hydrogen atom, a pharmaceutically acceptable cation, or a pharmaceutically acceptable group that that can be hydrolyzed in vivo, spotting 3 or more β-lactam agents differing in reactivity to metallo-β-lactamase, at positions different from the spot of the metallo-β-lactamase inhibitor, culturing the solid medium, and identifying the metallo-β-lactamase-producing bacteria based on a degree of inhibition affected by a presence of the metallo-β-lactamase inhibitor on each of the 3 or more β-lactam agents, wherein each of the 3 or more β-lactam agents has different reactivity to metallo-β-lactamases, and wherein the degree of inhibition is based on a shape of an inhibition zone determined by at least one value as an index selected from the minimum radius of the inhibition zone, a maximum radius of a inhibition zone, and a ratio between the minimum and maximum radiuses of the inhibition zone.

2. The method according to claim 1, wherein the 3 or more β-lactam agents differing in reactivity to metallo-β-lactamase comprise:
a β-lactam agent that is easily influenced by IMP metallo-β-lactamase but is not easily influenced by VIM metallo-β-lactamase;
a β-lactam agent that is easily influenced by both IMP metallo-β-lactamase and VIM metallo-β-lactamase; and
a cephem β-lactam agent that is easily influenced by IMP metallo-β-lactamase but is not easily influenced by VIM metallo-β-lactamase.

3. The method according to claim 2, wherein
the β-lactam agent that is easily influenced by IMP metallo-β-lactamase but is not easily influenced by VIM metallo-β-lactamase is biapenem or doripenem,
the β-lactam agent that is easily influenced by both IMP metallo-β-lactamase and VIM metallo-β-lactamase is imipenem or meropenem, and
the cephem β-lactam agent that is easily influenced by IMP metallo-β-lactamase but is not easily influenced by VIM metallo-β-lactamase is ceftazidime or cefepime.

4. The method according to claim 1, wherein the spot of each of the β-lactam agents is an equal distance from the spot of the metallo-β-lactamase inhibitor.

5. The method according to claim 1, wherein in the Formula (1), $R^1$ and $R^2$ are each a $C_{2-4}$ alkyl group.

6. The method according to claim 1, wherein in the Formula (1), $R^1$ and $R^2$ are each an ethyl group, and $M^1$ is a sodium cation or a potassium cation.

7. A method of identifying a type of metallo-β-lactamase-producing bacteria, comprising:
spotting a metallo-β-lactamase inhibitor represented by the following Formula (1) onto a surface of a solid medium coated with a bacteria to be tested,

[Formula 1]

wherein
$R^1$ represents a $C_{2-6}$ alkyl group, a $C_{3-7}$ cyclic alkyl group, a hydroxymethyl group, a —$C_{1-3}$ alkylene-phenyl group, a —$C_{0-1}$ alkylene-heterocyclic ring, a —O—$C_{1-6}$ alkyl group, or a —S—$C_{1-6}$ alkyl group, and each of these groups may have a substituent;

$R^2$ represents a $C_{1-6}$ alkyl group, a $C_{3-7}$ cyclic alkyl group, a hydroxymethyl group, a —$C_{1-3}$ alkylene-phenyl group, a —$C_{0-1}$ alkylene-heterocyclic ring, a —O—$C_{1-6}$ alkyl group, or a —S—$C_{1-6}$ alkyl group, and each of these groups may have a substituent; and each $M^1$, which may be the same or different, represent a hydrogen atom, a pharmaceutically acceptable cation, or a pharmaceutically acceptable group that can be hydrolyzed in vivo, spotting 3 or more β-lactam agents differing in reactivity to metallo-β-lactamase, at positions different from the spot of the metallo-β-lactamase inhibitor, culturing the solid medium, and identifying the type of the metallo-β-lactamase-producing bacteria based on a degree of inhibition affected by a presence of the metallo-β-lactamase inhibitor on each of the 3 or more β-lactam agents, wherein each of the 3 or more β-lactam agents has different reactivity to metallo-β-lactamases, and wherein the degree of inhibition is based on a shape of an inhibition zone determined by at least one value as an index selected from a minimum radius of the inhibition zone, a maximum radius of the inhibition zone, and a ratio between the minimum and maximum radiuses of the inhibition zone.

8. The method according to claim 7, wherein the 3 or more β-lactam agents differing in reactivity to metallo-β-lactamase comprise:
   a β-lactam agent that is easily influenced by IMP metallo-β-lactamase but is not easily influenced by VIM metallo-β-lactamase;
   a β-lactam agent that is easily influenced by both IMP metallo-β-lactamase and VIM metallo-β-lactamase; and
   a cephem β-lactam agent that is easily influenced by IMP metallo-β-lactamase but is not easily influenced by VIM metallo-β-lactamase.

9. The method according to claim 8, wherein
   the β-lactam agent that is easily influenced by IMP metallo-β-lactamase but is not easily influenced by VIM metallo-β-lactamase is biapenem or doripenem,
   the β-lactam agent that is easily influenced by both IMP metallo-β-lactamase and VIM metallo-β-lactamase is imipenem or meropenem, and
   the cephem β-lactam agent that is easily influenced by IMP metallo-β-lactamase but is not easily influenced by VIM metallo-β-lactamase is ceftazidime or cefepime.

10. The method according to claim 7, wherein the spot of each of the β-lactam agents is an equal distance from the spot of the metallo-β-lactamase inhibitor.

11. The method according to claim 7, wherein in the Formula (1), $R^1$ and $R^2$ are each a $C_{2-4}$ alkyl group.

12. The method according to claim 7, wherein in the Formula (1), $R^1$ and $R^2$ are each an ethyl group, and $M^1$ is a sodium cation or a potassium cation.

13. A kit for identification of a metallo-β-lactamase-producing bacteria, comprising:
   a substrate having three strips extended in different directions from a center;
   a disk disposed at the center of the substrate containing a metallo-β-lactamase inhibitor represented by the following Formula (1),

[Formula 1]

wherein
   $R^1$ represents a $C_{2-6}$ alkyl group, a $C_{3-7}$ cyclic alkyl group, a hydroxymethyl group, a —$C_{1-3}$ alkylene-phenyl group, a —$C_{0-1}$ alkylene-heterocyclic ring, a —O—$C_{1-6}$ alkyl group, or a —S—$C_{1-6}$ alkyl group, and each of these groups may have a substituent;
   $R^2$ represents a $C_{1-6}$ alkyl group, a $C_{3-7}$ cyclic alkyl group, a hydroxymethyl group, a —$C_{1-3}$ alkylene-phenyl group, a —$C_{0-1}$ alkylene-heterocyclic ring, a —O—$C_{1-6}$ alkyl group, or a —S—$C_{1-6}$ alkyl group, and each of these groups may have a substituent; and
   each $M^1$, which may be the same or different, represent a hydrogen atom, a pharmaceutically acceptable cation, or a pharmaceutically acceptable group that that can be hydrolyzed in vivo;
and
three disks respectively containing
   (A) a β-lactam agent that is easily influenced by IMP metallo-β-lactamase but is not easily influenced by VIM metallo-β-lactamase,
   (B) a β-lactam agent that is easily influenced by both IMP metallo-β-lactamase and VIM metallo-β-lactamase, and
   (C) a cephem β-lactam agent that is easily influenced by IMP metallo-β-lactamase but is not easily influenced by VIM metallo-β-lactamase,
   wherein each disk of the three disks is disposed on a separate strip of the three strips at an equal distance from the disk containing the metallo-β-lactamase inhibitor.

14. A method of identifying a metallo-β-lactamase-producing bacteria, comprising
   placing the kit according to claim 10 onto a surface of a solid medium coated with a bacteria to be tested,
   culturing the bacteria, and
   identifying the metallo-β-lactamase-producing bacteria based on a degree of inhibition affected by a presence of the metallo-β-lactamase inhibitor on each of the β-lactam agents,
   wherein the degree of inhibition is based on a shape of an inhibition zone determined by at least one value as an index selected from a minimum radius of the inhibition zone, a maximum radius of the inhibition zone, and a ratio between the minimum and maximum radiuses of the inhibition zone.

* * * * *